(12) United States Patent
Yamakawa et al.

(10) Patent No.: US 10,251,551 B2
(45) Date of Patent: Apr. 9, 2019

(54) FUNDUS ANALYSIS DEVICE AND FUNDUS ANALYSIS PROGRAM

(71) Applicant: NIDEK CO., LTD., Gamagori, Aichi (JP)

(72) Inventors: Ai Yamakawa, Gamagori (JP); Hisanari Torii, Gamagori (JP); Norimasa Satake, Gamagori (JP); Tetsuya Kano, Gamagori (JP); Ryoichi Aihara, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 180 days.

(21) Appl. No.: 15/032,123

(22) PCT Filed: Oct. 27, 2014

(86) PCT No.: PCT/JP2014/078477
§ 371 (c)(1),
(2) Date: Apr. 26, 2016

(87) PCT Pub. No.: WO2015/064531
PCT Pub. Date: May 7, 2015

(65) Prior Publication Data
US 2016/0302664 A1      Oct. 20, 2016

(30) Foreign Application Priority Data

Oct. 29, 2013    (JP) ................................ 2013-224302

(51) Int. Cl.
*A61B 3/00* (2006.01)
*A61B 3/14* (2006.01)
(Continued)

(52) U.S. Cl.
CPC .......... *A61B 3/1225* (2013.01); *A61B 3/0041* (2013.01); *A61B 3/102* (2013.01);
(Continued)

(58) Field of Classification Search
CPC ......... A61B 3/102; A61B 3/1225; A61B 3/12; A61B 3/0025; A61B 3/0058;
(Continued)

(56) References Cited

U.S. PATENT DOCUMENTS

2008/0024721 A1   1/2008   Ueno et al.
2009/0033870 A1   2/2009   Hangai et al.
(Continued)

FOREIGN PATENT DOCUMENTS

JP    2008-029467 A    2/2008
JP    2009-034480 A    2/2009
(Continued)

OTHER PUBLICATIONS

Oct. 31, 2017 Office Action issued in Japanese Patent Application No. 2013-224302.
(Continued)

*Primary Examiner* — Brandi N Thomas
(74) *Attorney, Agent, or Firm* — Oliff PLC

(57) ABSTRACT

A fundus analysis device includes: a first database which stores layer thickness information of fundus relating to a plurality of eyes having respective long ocular axial lengths; a processor; and memory storing non-transitory computer readable instructions, when executed by the processor, causing the fundus analysis device to execute: an acquisition instruction of acquiring a tomographic image of a fundus of an examinee's eye by an optical coherence tomography device; and an analysis processing instruction of acquiring analysis information relating to layer thickness information of the fundus of the examinee's eye by referring to the first database.

12 Claims, 6 Drawing Sheets

(51) Int. Cl.
  *A61B 3/12* (2006.01)
  *A61B 3/10* (2006.01)
  *G06T 7/00* (2017.01)
(52) U.S. Cl.
  CPC .......... *A61B 3/1005* (2013.01); *G06T 7/0014* (2013.01); *G06T 2207/10101* (2013.01); *G06T 2207/30041* (2013.01)
(58) Field of Classification Search
  CPC ......... A61B 3/0041; A61B 3/14; A61B 3/024; A61B 3/18; A61B 3/10; A61B 3/1005
  USPC ........ 351/200, 205, 206, 209–211, 221, 222, 351/243–245
  See application file for complete search history.

(56) References Cited

U.S. PATENT DOCUMENTS

| | | | |
|---|---|---|---|
| 2011/0170062 A1 | 7/2011 | Isogai et al. | |
| 2012/0281235 A1* | 11/2012 | Murata | A61B 3/102 356/479 |
| 2013/0188141 A1 | 7/2013 | Nakahara et al. | |
| 2013/0194546 A1 | 8/2013 | Iwase | |
| 2013/0195340 A1 | 8/2013 | Iwase et al. | |
| 2013/0258285 A1 | 10/2013 | Iwase et al. | |
| 2014/0112562 A1 | 4/2014 | Yamakawa et al. | |

FOREIGN PATENT DOCUMENTS

| | | |
|---|---|---|
| JP | 2009-089792 A | 4/2009 |
| JP | 2011-092702 A | 5/2011 |
| JP | 2012-016620 A | 1/2012 |
| JP | 2013-153844 A | 8/2013 |
| JP | 2013-153884 A | 8/2013 |
| JP | 2013-172941 A | 9/2013 |
| JP | 2013-208395 A | 10/2013 |
| JP | 2014-083268 A | 5/2014 |

OTHER PUBLICATIONS

Takahashi et al, "Retinal Thickness of Macula as Evaluated by Optical Coherence Tomography—Influence of Refractive Error and Axial Length", New Ophthalmic, Feb. 28, 2010, vol. 27, No. 2, pp. 270-273.
Takahashi Keiko et al., "Retinal Thickness of Macula as Evaluated by Optical Coherence Tomography—Influence of Refractive Error and Axial Length-," JCOPY, vol. 27, No. 2, (2010), pp. 132-135.
Jan. 20, 2015 Search Report issued in International Patent Application No. PCT/JP2014/078477.
May 3, 2016 International Preliminary Report on Patentability issued in International Patent Application No. PCT/JP2014/078477.

* cited by examiner

FUNDUS ANALYSIS DEVICE AND FUNDUS ANALYSIS PROGRAM

TECHNICAL FIELD

The present disclosure relates to a fundus analysis device and a fundus analysis program each for analyzing a tomographic image of a fundus of an examinee's eye.

BACKGROUND ART

Conventionally, a fundus analysis device that acquires a tomographic image of a fundus using an optical interference technique is known for evaluating a condition of an examinee's eye from the acquired tomographic image of the fundus (retina tomographic image) (see patent literature 1).

In this kind of fundus analysis device, a front fundus image acquired using infrared light is displayed on a monitor and a given region (portion) of the fundus image is selected. Then a fundus tomographic image of the selected area is acquired using the optical interference technique and temporarily stored in a storage unit (e.g., a hard disc) or the like of a personal computer. Thereafter the acquired fundus tomographic image is analyzed by the personal computer (PC) or the like and an analysis result is displayed on a monitor of the PC (see patent literature 2). An examiner looks the analysis result of the fundus tomographic image thus acquired and determines presence or absence of an abnormality of the examinee's eye.

CITATION LIST

Patent Literature

Patent Literature 1: JP-A-2008-29467
Patent Literature 2: JP-A-2011-92702

SUMMARY

Conventionally, the analysis result is acquired by comparing individual layers of the tomographic image of an examinee with a normal eye database storing thicknesses of individual layers of a normal eye. However in some cases, the thicknesses of individual layers of a fundus change depending on an ocular axial length. For example, in a case of acquiring an analysis result using the normal eye database with respect to the fundus tomographic image of an examinee having a long ocular axial length, there is a case that a difference between a thickness of each of the layers in the normal eye database and a thickness of corresponding one of the layers of the fundus tomographic image becomes large. In this case, it sometimes becomes difficult for an examiner to determine whether the large difference from the normal eye database is caused by the long ocular axial length of the examinee's eye or illness of the examinee.

Therefore, an aspect of the present disclosure, having been contrived in order to solve the heretofore described problem of the related art, has for its object to provide a fundus analysis device and a fundus analysis program each of which can provide information useful for supporting a diagnosis.

In order to solve the aforesaid problem, an aspect of the present disclosure is characterized by including the following configurations.

A fundus analysis device includes:
a first database which stores layer thickness information of fundus relating to a plurality of eyes having respective long ocular axial lengths;
a processor; and
memory storing non-transitory computer readable instructions, when executed by the processor, causing the fundus analysis device to execute:
an acquisition instruction of acquiring a tomographic image of a fundus of an examinee's eye by an optical coherence tomography device; and
an analysis processing instruction of acquiring analysis information relating to layer thickness information of the fundus of the examinee's eye by referring to the first database.

A non-transitory computer readable recording medium stores a fundus analysis program executed by a processor of a fundus analysis device which includes a database which stores layer thickness information of fundus relating to a plurality of eyes having respective long ocular axial length, the program, when executed by the processor, causing the fundus analysis device to execute:
an acquisition instruction of acquiring a tomographic image of a fundus of an examinee's eye acquired by an optical coherence tomography device; and
analysis processing instruction of acquiring analysis information relating to layer thickness information of the fundus of the examinee's eye by referring to the database.

According to the aspect of the present disclosure, information useful for a diagnosis can be provided.

DESCRIPTION OF EMBODIMENTS

Summary

Figure 1:
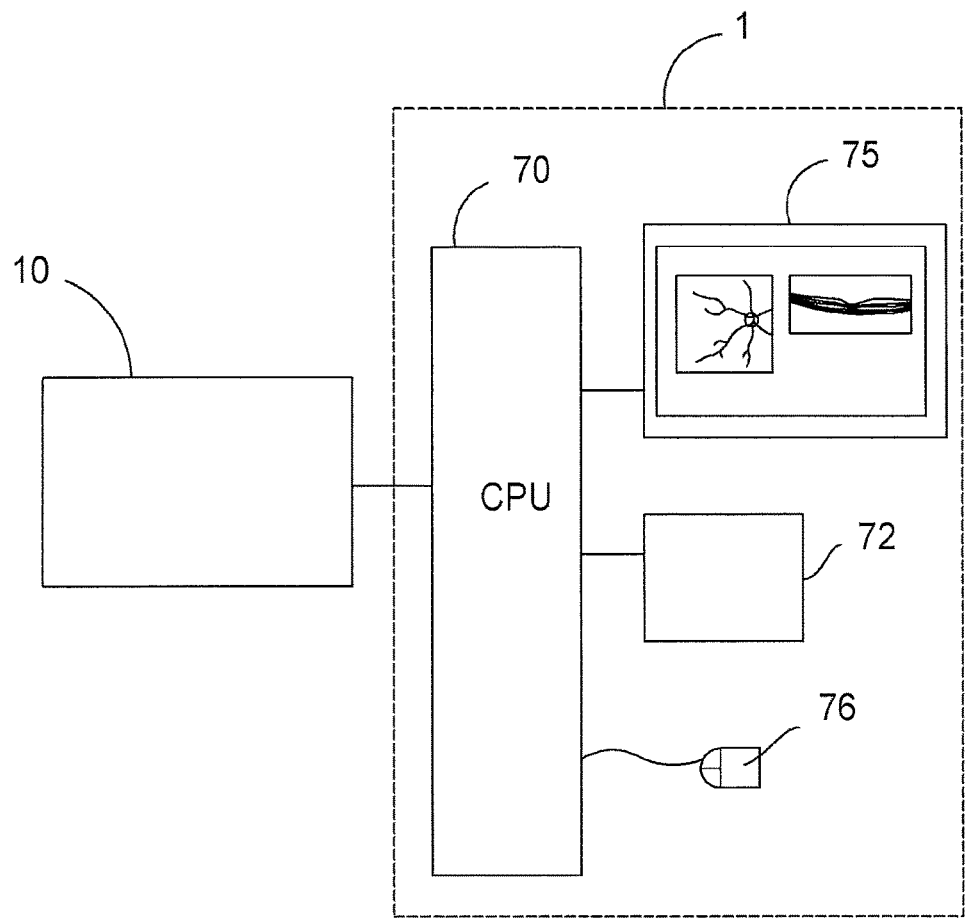
FIG. 1 is a block diagram for explaining configuration of a fundus analysis device according to an embodiment.

Hereinafter one of typical embodiments will be explained with reference to drawings. FIGS. 1 to 7 are diagrams for explaining an apparatus and a program according to the embodiment. In the following explanation, an axial direction (front-to-rear direction) of an examinee's eye E is referred to as a Z-direction, a horizontal direction (left-to-right direction) is referred to as an X-direction, and a vertical direction (up-down direction) is referred to as a Y-direction. A direction along the surface of a fundus may be referred to as an XY-direction.

A fundus analysis device 1 according to the embodiment acquires a tomographic image using a fundus photographing device (e.g., an optical coherence tomography device (OCT device)) 10 for acquiring a tomographic image of a fundus of an examinee's eye, then processes the acquired tomographic image and acquires layer thickness information of the fundus of the examinee's eye.

For example, the fundus analysis device 1 may be connected to the fundus photographing device 10 for photographing an image at a given portion of an examinee's eye. Alternatively, for example, the fundus analysis device 1 may be integrated with the fundus photographing device.

For example, the fundus analysis device 1 is constituted of a CPU (arithmetic control unit) 70, a mouse (operation unit) 76, a nonvolatile memory (storage unit) 72, and a monitor 75. These units are electrically connected to the arithmetic control unit (control unit) 70 via buses, and so on. Incidentally, the operation unit is not limited to the mouse but an interface such as a keyboard or a touch panel may be used.

In this embodiment, for example, the analysis processing means (control unit) 70 acquires analysis information relating to layer thickness information of a fundus of an examinee's eye by referring to a first database which stores layer thickness information of fundus of plural eyes having respective long ocular axial lengths. By doing so, for example, an examiner can more accurately diagnose whether a large difference from the normal eye database is caused by a long ocular axial length of the examinee's eye or illness of the examinee.

An example of the analysis information is an analysis map, an analysis chart, a deviation map or the like. An example of the analysis map is a comparison map, a difference map or the like. For example, the comparison map represents a results of comparison between thickness of a retina layer of the examinee's eye and a thickness of a retina layer of a predetermined examinee's eye stored in the normal eye database. Further, for example, the difference map represents a results of a difference between the thickness of the retina layer of the examinee's eye and the thickness of the retina layer of the predetermined examinee's eye stored in the normal eye database.

The analysis information relating to the layer thickness information of the fundus of the examinee's eye may be information relating to a distance (layer thickness) of layer boundaries corresponding to a predetermined retina layer (e.g., a retina surface and a pigmented layer of the retina). Incidentally the analysis information is not limited to the retina layer. For example, the analysis information may be analysis information relating to a choroid layer or analysis information of an entire fundus containing the retina layer and the choroid layer.

In this embodiment, in addition to the first database which stores the layer thickness information of the fundus relating to plural eyes having the respective long ocular axial lengths, a second database which stores thickness information of retina layers relating to plural examinees' eyes each of which at least differs in an ocular axial length from the first database may be provided. For example, a long ocular axial length database and a normal eye database or the like are used as the first database and the second database, respectively. The first database may be prepared by integrating data of plural examinees' eyes having respective ocular axial lengths each exceeding a reference threshold. In contrast, the second database may be prepared by integrating data of plural examinees' eyes each having an ocular axial length not exceeding the reference threshold. Incidentally, the first database may store statistical characteristic information acquired from the data of examinees' eyes having the respective ocular axial lengths each exceeding the reference threshold. In contrast, the second database may store statistical characteristic information acquired from the data of examinees' eyes each having the ocular axial length not exceeding the reference threshold.

For example, the control unit 70 may control switching between the first database and the second database when a reception means receives a database switch signal. The control unit 70 may acquire the analysis information relating to the layer thickness information of the fundus of an examinee's eye by referring to at least one of the first and second databases. By doing so, for example, the examiner can acquire the analysis information according to various ocular axial lengths. Further, for example, as the examiner can acquire the analysis information using a plurality of the databases, the examiner can perform a diagnosis by taking more information into consideration.

For example, as the configuration for switching the database, the control unit 70 may be configured to control the switching between the first and second databases by receiving the database switch signal which is outputted when the examiner operates the operation unit 76. For example, the operation of the operation unit 76 performed by the examiner is inputting of an ocular axial length value. In this case, for example, a switch signal output means may output the database switch signal based on the ocular axial length value, and the switching of the database may be controlled when the reception means receives the database switch signal. Further, for example, the operation of the operation unit 76 performed by the examiner is a selection of a database changeover switch. In this case, the switch signal output means may output the database switch signal when the database changeover switch is selected, and the switching of the database may be controlled when the reception means receives the database switch signal. Incidentally, in the embodiment, the control unit 70 also serves as the switch signal output means and the reception means. Of course, the switch signal output means and the reception means may be provided independently from the control unit.

As the configuration for switching between the databases, for example, the control unit 70 may be configured to be connected to an ocular axial length measurement apparatus and receive an ocular axial length value measured by the ocular axial length measurement apparatus. Alternatively, for example, the control unit 70 may be configured to acquire an ocular axial length of an examinee from a memory or a device which stores ocular axial length values. In this case, for example, the switch signal output means may output the database switch signal based on an ocular axial length value, and the switching of the database may be controlled when the reception means receives the database switch signal. Incidentally, in the embodiment, the control unit 70 also serves as the switch signal output means and the reception means.

For example, the control unit 70 may change a display mode on the monitor 75 when the switching is performed between the first and second databases. For example, as the monitor 75, a monitor of an external PC or a monitor unitedly provided with the fundus photographing device 10 or the fundus analysis device 1 may be employed.

For example, configuration for changing the display mode is configuration for changing a size of the analysis map. Alternatively, for example, in a case where the database is switched, the control unit 70 may change a display (change of a color, change of a character size, display of a mark of the corresponding database, or the like) so that the database which is referred to upon acquiring the analysis information can be identified. Alternatively, for example, the control unit

70 may change a parameter concerning the analysis information. By doing so, for example, as the display of the analysis information is changed in accordance with the switching of the database, the examiner can easily confirm a current analysis condition.

Although the control unit 70 is configured to change the display mode of the monitor when the switching is performed between the first and second databases, the control unit is not limited to this configuration. For example, the control unit 70 is merely required to add identification information, for identifying one of the first and second databases having been referred to, in the analysis information in a case where the switching is performed between the first and second databases. For example, the control unit 70 may change and output the display (change of a color, change of a character size, display of a mark of the corresponding database, or the like) so that the database which is referred to upon acquiring the analysis information can be identified. For example, this output is supplied to a printer (printing machine) or the monitor. By doing so, for example, as the examiner is not required to newly confirm the analysis condition, labor, load, etc. of the examiner can be lightened. Further, it can be suppressed that the analysis information is acquired using the database different from that intended by the examiner.

In this embodiment, for example, the control unit 70 may detect, via an image processing, layer information in three-dimensional OCT data of the fundus of the examinee's eye acquired by the optical coherence tomography device, and acquire an analysis map representing a two-dimensional distribution relating to the layer thickness information of the fundus of the examinee's eye by referring to the first database or the second database. For example, the control unit 70 may switch the database when the reception means receives the database switch signal outputted based on an ocular axial length value. The control unit 70 may display a front image of the fundus of the examinee's eye acquired by a front image acquisition means and the analysis map in a superimposed manner and change the size of the analysis map with respect to the front image.

For example, the front image acquisition means (front observation optical system) 200 may be provided at the OCT device 10 in order to acquire a front image of a fundus Ef. For example, the front observation optical system (observation optical system) 200 is an ophthalmic scanning laser ophthalmoscope (SLO), a fundus camera type or the like. Further, for example, the observation optical system 200 may be arranged to acquire the front image using data forming a tomographic image obtained two-dimensionally (e.g., an integrated image of three-dimensional tomographic images in a depth direction, an integrated value of spectral data at individual positions in the XY-direction, luminance data at individual positions in the XY-direction in a certain constant depth direction, a retinal surface layer image, or the like).

The technique disclosed in this embodiment may be applied to a single tomographic image. In this case, the control unit 70 may acquire a plurality of the analysis information with respect to the single tomographic image by referring to a plurality of the databases. For example, with respect to the single tomographic image of the examinee's eye, the control unit 70 may acquire first analysis information relating to the layer thickness information of the fundus of the examinee's eye by referring to the first database, and may acquire second analysis information relating to the layer thickness information of the fundus of the examinee's eye by referring to the second database. The control unit 70 may display the first analysis information relating to the layer thickness information of the fundus of the examinee's eye and the second analysis information relating to the tomographic image on the same screen of the monitor 75. By doing so, for example, the examiner can diagnose the examinee's eye using various kinds of diagnosis support tools and hence can perform a diagnosis easily.

Incidentally, the technique disclosed in this embodiment can also be applied to a case where an observation is performed by changing the database at a time of follow-up. For example, the control unit 70 may acquire a plurality of the layer thickness information of the fundus of the examinee's eye obtained by photographing the tomographic image of the same examinee's eye at different timings, and acquire a plurality of the analysis information respectively corresponding to the plurality of layer thickness information by referring to at least one of the first and second databases. The control unit 70 may display the plurality of analysis information on the same screen of the monitor.

For example, the control unit 70 may acquire the first analysis information by referring to the first database with respect to the first layer thickness information of the fundus of the examinee's eye, and acquire the second analysis information by referring to the second database with respect to the second layer thickness information of the fundus of the examinee's eye which is different in an acquisition timing of the tomographic image from that of the first layer thickness information. For example, the control unit 70 may display, on the same screen of the monitor, the first analysis information acquired by referring to the first database with respect to the first layer thickness information of the fundus of the examinee's eye and the second analysis information acquired by referring to the second database with respect to the second layer thickness information of the fundus of the examinee's eye which is different in the acquisition timing of the tomographic image from that of the first layer thickness information. This can be applied not only to a case of outputting two analysis information different in the acquisition timing of the tomographic image but also to a case of outputting at least three analysis information different in the acquisition timing of the tomographic image. With such the configuration, for example, even if the ocular axial length changes in a case of photographing on a different date, the diagnosis can be performed in a state of being coped with the change of the ocular axial length. Further, for example, continuous observation becomes possible also with respect to the examinee's eye which is conventionally difficult to be observed continuously due to a fact that good analysis information cannot be acquired according to the change of ocular axial length. In this embodiment, the fundus analysis device may further include an ocular axial length value acquisition means which acquires an ocular axial length value. The ocular axial length value acquisition means may be the control unit 70 which is arranged to acquire the ocular axial length value via the operation unit 76 that can input the ocular axial length value by an operation of the examiner. Alternatively, the ocular axial length value acquisition means may be the control unit 70 which is arranged to acquire the ocular axial length value of the examinee's eye from a memory or a device storing the ocular axial length value. The control unit 70 may perform switching between the first and second databases based on the acquired ocular axial length value. With such the configuration, the fundus analysis device can suitably select the database according to the ocular axial length value.

Incidentally, the invention is not limited to the apparatus described in the embodiment. For example, fundus analysis software (program) executing the functions of the embodiment may be supplied to the system or the apparatus via a network or one of various kinds of storage media or the like. Then a computer (e.g., a CPU) of the system or the apparatus can also read and execute the program.

Embodiment

Hereinafter a typical embodiment will be explained with reference to drawings. FIG. 1 is a block diagram for explaining configuration of the fundus analysis device according to the embodiment.

The fundus analysis device 1 is used so that a fundus image photographed by the fundus photographing device (e.g., an optical coherence tomography device (OCT device)) is observed on the monitor. As an example, the fundus analysis device 1 is constituted of the CPU (arithmetic control unit) 70, the mouse (operation unit) 76, the nonvolatile memory (storage unit) 72, and the monitor 75. These units are electrically connected to the arithmetic control unit (control unit) 70 via buses, and so on.

Incidentally, the fundus analysis device 1 is connected to the fundus photographing device 10 for photographing an image at a given portion of an examinee's eye. In this embodiment, as an example, the OCT device 10 for photographing a tomographic image of a fundus Ef of an examinee's eye E will be explained as the fundus photographing device. In this embodiment, although the fundus analysis device 1 is connected to the fundus photographing device 10, the configuration of the embodiment is not limited thereto. The fundus analysis device 1 may be integrated with the fundus photographing device.

Figure 2:
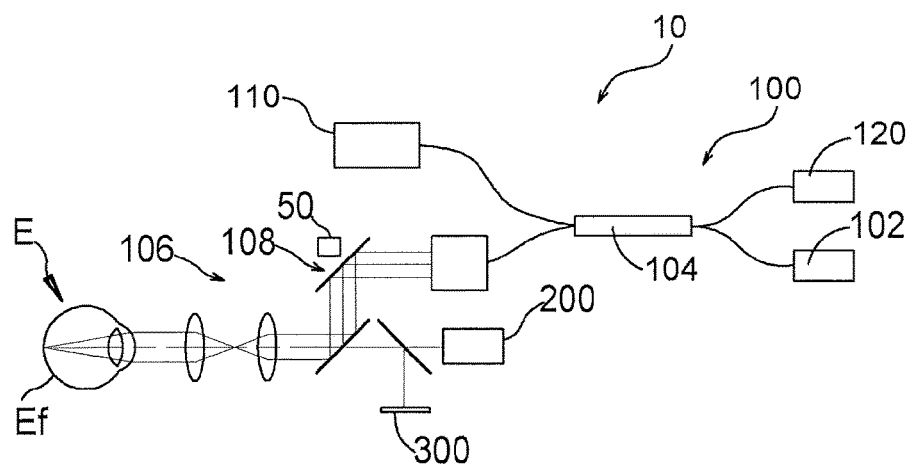
FIG. 2 is a schematic configuration diagram for explaining configuration of a fundus photographing device according to the embodiment.

FIG. 2 is a schematic configuration diagram for explaining configuration of the fundus photographing device according to the embodiment. Hereinafter the schematic configuration of the device will be explained using FIGS. 1 and 2. This fundus photographing device is the fundus photographing device 10 for photographing a tomographic image of the fundus Ef of the examinee's eye E. The fundus photographing device 10 mainly includes an interference optical system (OCT optical system) 100, and may further include the front observation optical system 200 and a fixation target projection unit 300. The fundus photographing device 10 is connected to the control unit 70. That is, the fundus analysis device 1 is connected to the fundus photographing device 10.

The OCT optical system 100 irradiates a measurement light onto a fundus. The OCT optical system 100 detects an interference state between the measurement light reflected from the fundus and a reference light using a light receiving element (detector 120). In order to change a photographing position on the fundus Ef, the OCT optical system 100 includes an irradiation position change unit (e.g., an optical scanner 108, the fixation target projection unit 300) arranged to change the irradiation position of the measurement light on the fundus Ef. The control unit 70 controls an operation of the irradiation position change unit based on photographing position information being set and acquires a tomographic image based on a light reception signal from the detector 120.

<OCT Optical System>

The OCT optical system 100 has a device configuration of a so-called ophthalmic optical coherence tomography (OCT: Optical coherence tomography) and photographs the tomographic image of the eye E. The OCT optical system 100 splits a light emitted from a measurement light source 102 into the measurement light (sample light) and the reference light using a coupler (optical splitter) 104. Then the OCT optical system 100 conducts the measurement light to the fundus Ef of the eye E via a measurement optical system 106 and also conducts the reference light to a reference optical system 110. Thereafter the detector (light receiving element) 120 receives an interference light composed by the measurement light reflected from the fundus Ef and the reference light.

The detector 120 detects the interference state between the measurement light and the reference light. In a case of a Fourier-domain OCT, a spectral intensity of the interference light is detected by the detector 120, and a depth profile (A scan signal) in a predetermined range is acquired by performing a Fourier transform on the spectral intensity data. Such the OCT optical system is, for example, a spectral-domain OCT (SD-OCT) or a swept-source OCT (SS-OCT). Alternatively, such the OCT optical system may be a time-domain OCT (TD-OCT).

In the case of the SD-OCT, a low-coherence light source (wide band light source) is used as the light source 102, and a spectroscopic optical system (spectrometer) for spectrally dispersing the interference light into individual frequency components (individual wavelength components) is provided as the detector 120. The spectrometer is constituted of, for example, a diffraction grating and a line sensor.

In the case of the SS-OCT, a wavelength scanning light source (wavelength variable light source) for changing a wavelength of emission light at a temporarily high speed is used as the light source 102, and a single light receiving element, for example, is used as the detector 120. The light source 102 is constituted of, for example, a light source, a fiber ring resonator and a wavelength selection filter. An example of the wavelength selection filter is a combination of a diffraction grating and a polygon mirror or a Fabry-Perot etalon.

Light emitted from the light source 102 is split into the measurement light beam and the reference light beam by the coupler 104. The measurement light beam passes an optical fiber and is irradiated in the air. Then this light beam is focused on the fundus Ef via the optical scanner 108, the measurement optical system 106 and other optical members. Light reflected from the fundus Ef returns to the optical fiber via the same optical path.

The optical scanner 108 scans the measurement light two-dimensionally (in the XY-direction (transverse direction)) on the fundus. The optical scanner 108 is disposed at a position substantially conjugate with a pupil. The optical scanner 108 is constituted of, for example, two galvano mirrors. A reflection angle of the galvano mirror is adjusted optionally by a driving mechanism 50.

By doing so, the light beam emitted from the light source 102 is changed in its reflection (traveling) direction and scanned in an optional direction on the fundus. In this manner, the photographing position on the fundus Ef is changed. The optical scanner 108 is merely required to be configured to deflect the light. For example, as the optical scanner, a reflection mirror (galvano mirror, polygon mirror, resonant scanner), an acoustic optical element (AOM) for changing the travelling (deflection) direction of the light, or the like is used.

The reference optical system 110 generates the reference light which is composed with the reflection light which is obtained from the measurement light reflected from the fundus Ef. The reference optical system 110 may be a Michelson type or a Mach-Zehnder type. The reference optical system 110 is, for example, constituted of a reflection optical system (e.g., reference mirror) so that the light from the coupler 104 is reflected by the reflection optical system and returned to the coupler 104 and then conducted to the detector 120. As another example, the reference optical system 110 is constituted of a transmission optical system (e.g., optical fiber) which transmits the light from the coupler 104 without returning and conducts to the detector 120.

The reference optical system 110 has a configuration of changing an optical length difference between the measurement light and the reference light by moving an optical member within a reference optical path. For example, the reference mirror is moved in an optical axis direction. The configuration for changing the optical length difference may be arranged in a measurement optical path of the measurement optical system 106.

<Front Observation Optical System>

The front observation optical system 200 is provided in order to acquire the front image of the fundus Ef. The observation optical system 200 includes an optical scanner arranged to scan the measurement light (e.g., infrared light) emitted from the light source two-dimensionally on the fundus, and a second light receiving element arranged to receive the light reflected from the fundus through a confocal opening disposed at a position substantially conjugate with the fundus. Accordingly, the observation optical system has the configuration of the so-called ophthalmic scanning laser ophthalmoscope (SLO).

For the configuration of the observation optical system 200, a so-called fundus camera type configuration may be used. The OCT optical system 100 may also serve as the observation optical system 200. In other words, the front image may be acquired using the data forming the tomographic image obtained two-dimensionally (e.g., an integrated image of the three-dimensional tomographic images in the depth direction, an integrated value of the spectral data at individual positions in the XY-direction, luminance data at individual positions in the XY-direction in a certain constant depth direction, a retinal surface layer image, or the like).

<Fixation Target Projection Unit>

The fixation target projection unit 300 includes an optical system arranged to lead a sight line direction of the eye E. The projection unit 300 has a fixation target which is presented to the eye E and can guide the eye E in plural directions.

For example, the fixation target projection unit 300 has a visible light source generating a visible light and changes the presentation position of the target two-dimensionally. By doing so, the sight line direction is changed, and consequently the photographing position is changed. For example, if the fixation target is presented from the same direction as that of a photographing optical axis, the center portion of the fundus is set as the photographing position. Further, if the fixation target is presented above with respect to the photographing optical axis, an upper portion of the fundus is set as the photographing position. In this manner, the photographing position is changed according to the position of the target with respect to the photographing optical axis.

As the fixation target projection unit 300, it is considered to selectively employ various kinds of configurations such as a configuration of adjusting the fixation position according to a lighting position of LEDs arranged in a matrix fashion, and a configuration of scanning light from the light source using the optical scanner and adjusting the fixation position according to lighting control of the light source. The fixation target projection unit 300 may be an internal fixation lamp type or an external fixation lamp type.

<Control Unit>

The control unit 70 includes the CPU (processor), an RAM, an ROM, etc. The CPU of the control unit 70 controls the entirety of the apparatus (fundus analysis device 1, fundus photographing device 10) such as the individual members of the individual configurations 100 to 300. The RAM temporarily stores various kinds of information. The ROM of the control unit 70 stores various kinds of programs for controlling operations of the entirety of the apparatus and initial values, etc. Incidentally, the control unit 70 may be configured by a plurality of control units (i.e., a plurality of processors).

The control unit 70 is electrically connected to the nonvolatile memory (storage means) 72, the operation unit (control part) 76, the display unit (monitor) 75, and so on. The nonvolatile memory (memory) 72 is a non-temporary storage medium which can hold storage content even if power feed from a power source is interrupted. For example, a hard disc drive, a flash ROM, a USB memory detachably attached to the fundus analysis device 1 and the fundus photographing device 10, or the like can be used as the nonvolatile memory 72. The memory 72 stores a photographing control program for controlling the photographing of the front image and the tomographic image performed by the fundus photographing device 10. Further the memory 72 stores a fundus analysis program enabling the use of the fundus analysis device 1. Further the memory 72 stores various kinds of information relating to the photographing such as information of the photographing positions of the front image and tomographic image of the fundus. Various kinds of operation instructions are inputted into the operation unit 74 by the examiner.

The operation unit 76 outputs a signal according to the inputted operation instruction to the control unit 70. For example, at least one of a mouse, a joystick, a keyboard, a touch panel, etc. may be used as the operation unit 74.

The monitor 75 may be a display mounted in a main body of the fundus photographing device 10 or a display connected to the main body. A display of the personal computer (hereinafter referred to as "PC") may be used as the monitor. A plurality of the displays may be used together. Alternatively, the monitor 75 may be a touch panel. If the monitor 75 is the touch panel, the monitor 75 acts as the operation unit. The monitor 75 displays various kinds of images including the tomographic image and the front image photographed by the fundus photographing device 10.

<Acquisition of Tomographic Image>

Hereinafter a photographing operation of this apparatus will be explained. Firstly the fundus photographing device 10 acquires the tomographic image. The examiner instructs the examinee to notice the fixation target of the fixation target projection unit 300. Thereafter the examiner performs an alignment operation using the operation unit 76 (e.g., not-shown joystick) so that the measurement optical axis locates at the center of the pupil of the examinee's eye while looking an anterior-eye observation image photographed by a not-shown anterior-eye observation camera on the monitor 75.

The control unit 70 controls driving of the optical scanner 108 so as to scan the measurement light in a predetermined direction on the fundus, then acquires a light reception signal corresponding to a predetermined scanning area from an output signal outputted from the detector 120 during the scanning and forms a tomographic image. Further, the control unit 70 acquires the tomographic image by controlling the OCT optical system 100 and acquires a front image of the fundus by controlling the observation optical system 200. Then the control unit 70 occasionally acquires the tomographic image via the OCT optical system 100 and the front fundus image (front image) via the observation optical system 200. By doing so, the tomographic image and the front fundus image are displayed on the screen of the monitor 75.

In this embodiment, a three-dimensional tomographic image is acquired via the OCT optical system 100 and then analyzed. In a case of acquiring the three-dimensional tomographic image, the examiner operates the operation unit 76 and sets the scanning position using the front fundus image acquired via the observation optical system 200. Then the examiner operates the operation unit 76 and selects a not-shown photographing switch. When a signal starting the photographing is outputted from the operation unit 76, the control unit 70 controls the operation of the optical scanner 108, thereby scanning the measurement light in the XY-direction two-dimensionally in a scanning range corresponding to a photographing area and acquiring the three-dimensional tomographic image. Incidentally, as the scanning pattern, for example, a later scanning, a plurality of line scanning or the like may be used. The three-dimensional tomographic image is, for example, image data of A scan signals arranged two-dimensionally in the XY-direction or a three-dimensional graphic image.

The control unit 70 stores the three-dimensional tomographic image and the front fundus image thus acquired in the memory 72. When the examiner operates the operation unit 76 and selects an analysis mode switch on the screen of the monitor 75, the control unit 70 switches the mode. In the analysis mode, the control unit 70 performs an analysis processing of the three-dimensional tomographic image stored in the memory 72 and acquires the analysis information. The switching to the analysis mode may be achieved by such a configuration that the switching is performed automatically after the tomographic image is acquired by the fundus photographing device 10. In this case, for example, the control unit 70 stores the acquired tomographic image in the memory 72 and also performs the switching to the analysis mode.

<Analysis Mode>

After performing the switching to the analysis mode, the control unit 70 detects, via the image processing, the layer information of the fundus in the acquired tomographic image (e.g., three-dimensional tomographic image). The control unit 70 analyzes the detection results of the individual layers by referring to the normal eye database (details will be described later) and acquires the analysis information. Then the analysis information is stored together with the tomographic image in the memory 72 or an external memory (e.g., a memory of the personal computer or a memory of a server). Further the control unit 70 displays, together with the tomographic image, the analysis information stored in the memory 72 on the screen of the monitor 75. Of course, the control unit 70 may be configured to display at least one of the analysis information and the tomographic image as the image displayed on the screen of the monitor 75.

An example of the analysis information is the analysis map, the analysis chart, the deviation map or the like. An example of the analysis map is the comparison map, the difference map or the like. The comparison map represents the result of comparison between the thickness of the retina layer of the examinee's eye and the thickness of the retina layer of the predetermined examinee's eye stored in the normal eye database (details will be described later). The difference map represents the result of difference between the thickness of the retina layer of the examinee's eye and the thickness of the retina layer of the predetermined examinee's eye stored in the normal eye database. Incidentally the analysis information is not limited to analysis information relating to the retina layer but may be analysis information relating to the choroid layer. Alternatively the analysis information may be analysis information relating to the entirety of the fundus containing the retina layer and the choroid layer.

Further, for example, the deviation map is a map representing a ratio which is obtained by dividing a difference between the thickness of the retina layer of the examinee's eye and the thickness of the retina layer of the predetermined examinee's eye stored in the normal eye database, by the thickness of the retina layer of the predetermined examinee's eye stored in the normal eye database. Alternatively, for example, the deviation map is a map representing, as a standard deviation, the difference between the thickness of the retina layer of the examinee's eye and the thickness of the retina layer of the predetermined examinee's eye stored in the normal eye database.

Further, for example, the analysis chart (see an analysis charts in FIG. 7) is a chart showing an analysis value for each section set in advance. The control unit 70 may acquire, as the analysis value, a basic statistic of the analysis result for each the section set in advance. An example of the basic statistic may be a representative value (average value, center value, mode, maximum value, minimum value or the like), a dispersion (variance, standard deviation, variation coefficient) or the like. More specifically, the analysis chart may be a chart showing a representative value (e.g., average value, center value) of the analysis result for each the section set in advance. Alternatively, the analysis chart may be a chart showing a maximum value or a minimum value of the analysis result for each the section set in advance. As the analysis result for each the section contains analysis results at individual positions within the section, stable analysis values can be obtained.

This embodiment will be explained, for example, as to a case of acquiring the comparison map as the analysis information. For example, the control unit 70 detects a luminance level of the tomographic image in a case of detecting the layer. The control unit 70 extracts, via an image processing, layer boundaries corresponding to a predetermined retina layer (e.g., a retina surface and a pigmented layer of the retina). Then the control unit 70 acquires layer thickness (thickness of layer) information by measuring an interval of the layer boundaries. Incidentally in this embodiment, although the comparison map is used as the analysis information, the configuration of the embodiment is not limited thereto. For example, other analysis information may be acquired as the analysis information. Further a plurality of analysis information may be acquired.

The control unit 70 acquires the layer thickness information at individual positions in the XY-direction and acquires the analysis information relating to the layer thickness referring to the normal eye database. Of course, a sum of a plurality of the layer thicknesses may be employed in the analysis using the layer thickness.

For example, as the normal eye database, characteristic information (intervals of the individual layers, shape and size of a predetermined portion, etc.) of examinees' eyes regarded to be normal may be stored. The normal eye database may be prepared by integrating data of plural examinees' eyes. For example, as the normal eye database, statistical characteristic information acquired from the data of the plural examinees' eyes may be stored.

For example, in a case of acquiring the analysis information relating to the layer thickness, the control unit 70 acquires the analysis information using the intervals of the individual layers stored at least in the database. For example, as to the information of the intervals of the individual layers in the normal eye database, a range of the layer thickness regarded to be normal, a range of the layer thickness regarded to be a border line of the normal, a range of the layer thickness regarded to be abnormal, and so on are stored as the information relating to the layer thickness.

For example, the control unit 70 determines, with respect to each of the individual positions, a range of the layer thickness in the normal eye database to which the layer thickness information of a certain position belong. The control unit 70 acquires the comparison map based on the determination result by referring to the normal eye database.

Figure 3:
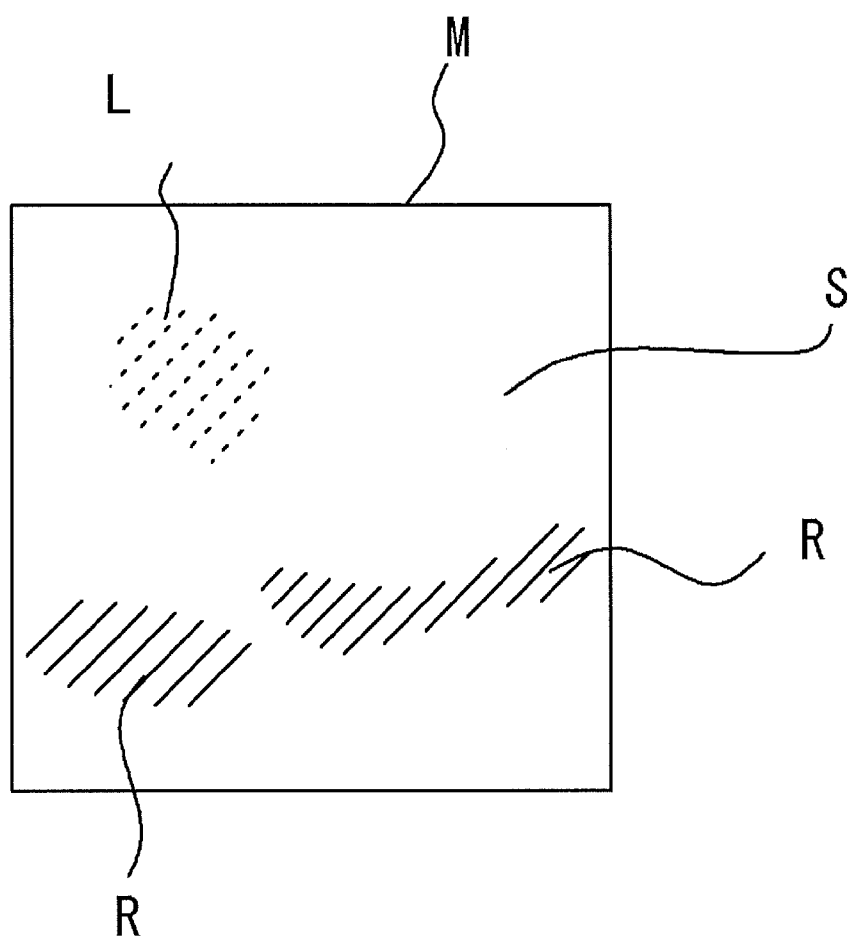
FIG. 3 is a diagram illustrating an example of a comparison map.

In this embodiment, the control unit 70 prepares, as the comparison map, a map (e.g., camera map) graphically illustrating the analysis information of three-dimensional tomographic image, based on the determination result. FIG. 3 is a diagram illustrating an example of the comparison map M. For example, as shown in FIG. 3, the comparison map M graphically represents a normal portion S, a border line portion (see a steady-line hatched portion R) and an abnormal portion (see a dotted-line hatched portion L) according to the comparison result between the layer thicknesses of the retina layer of the examinee's eye and the layer thickness stored in the normal eye database. For example, the hatched portions R and L are displayed by particular colors (e.g., red and yellow or the like), respectively. In this embodiment, the normal portion S is displayed by green. Further, in this embodiment, the border line portion R is displayed by yellow. Further, in this embodiment, the abnormal portion L is displayed by red.

Incidentally although this embodiment is configured to represent the comparison result by the particular colors, the embodiment is not limited thereto. The comparison result is merely required to be graphically displayed in a distinguishable manner. For example, the control unit 70 may surround each of the border line portion and the abnormal portion by a marker. The analysis information is acquired in this manner.

The normal eye database is constituted of data obtained from data of the examinees' eyes regarded to be normal. For example, the examinees' eyes satisfying a predetermined condition is employed at the time of preparing the normal eye database. For example, as the predetermined condition, a range of an average ocular axial length value (e.g., ocular axial length of less than 26 mm) of the examinees' eyes is set. In other words, the normal eye database is applicable only to an examinee's eye having the ocular axial length value within a predetermined ocular axial length range. Thus if the normal eye database is referred to with respect to an examinee's eye having an ocular axial length value outside the predetermined ocular axial length range, which results in reduction of reliability of the analysis information. For example, if an ocular axial length of an examinee's eye extends, a thickness of the retina layer of the fundus may be thinner. In this case, if the normal eye database is referred to, there may arise a case that a difference between a thickness of each of the layers in the normal eye database and a thickness of corresponding one of the tomographic mage of the fundus becomes large. In this case, it becomes difficult for the examiner to determine whether a large difference from the normal eye database is caused by the long ocular axial length of the examinee's eye or illness of the examinee.

This embodiment includes a long ocular axis database storing characteristic information (e.g., layer thickness information) of examinees' eyes having individual ocular axial lengths (e.g., ocular axial length of 26 mm or more). In this embodiment, as the database, the normal eye database and the long ocular axis database are stored in the memory 72. For example, the control unit 70 performs the switching between the normal eye database and the long ocular axis database. The control unit 70 acquires the analysis information relating to the layer thickness information of the fundus of the examinee's eye by referring to at least one of these databases.

The long ocular axis database may be, for example, a database which is prepared supposing the analysis of an examinee's eye having an ocular axial length longer than the applicable range of the normal eye database (e.g., ocular axial length of 26 mm or less). More in detail, the long ocular axis database may store, with respect to examinees' eyes having respective ocular axial lengths each exceeding a reference threshold value (e.g., 26 mm), characteristic information (intervals of the individual layers, shape and size of a predetermined portion, etc.) of examinees' eyes regarded to be normal.

The long ocular axis database may be prepared, for example, by integrating data of plural examinees' eyes having respective ocular axial lengths each exceeding the reference threshold value (e.g., 26 mm). The long ocular axis database may store, for example, statistical characteristic information obtained from data of examinees' eyes.

Incidentally, preferably, the applicable ranges of the normal eye database and the long ocular axis database are clearly distinguished with respect to the reference threshold value as a boundary, but the embodiment is not limited thereto. For example, these applicable ranges may be overlapped partially near the boundary of these applicable ranges.

Figure 4:
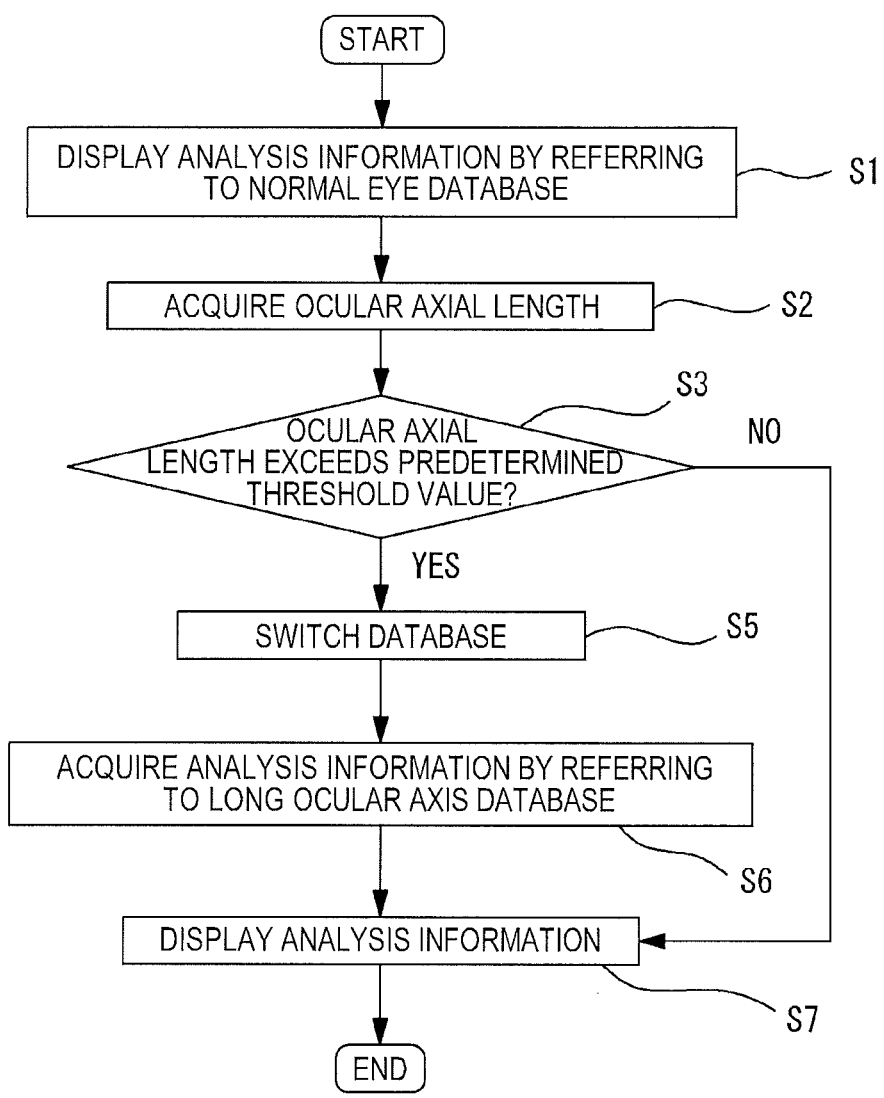
FIG. 4 is a flowchart for explaining a flow of an example of a control operation in an analysis mode.

FIG. 4 is a flowchart for explaining a flow of an example of a control operation in the analysis mode. The control unit 70 executes the control of the flowchart in FIG. 4. Hereinafter the control operation in the analysis mode will be explained with reference to FIG. 4. For example, in this embodiment, in a case where the ocular axial length value is not inputted in advance before performing the switching to the analysis mode, the control unit 70 acquires the analysis information (comparison map in this embodiment) referring to the normal eye database upon the switching to the analysis mode. Then the control unit 70 displays the comparison map on the front fundus image in a superimposed manner (S1).

Figure 5:
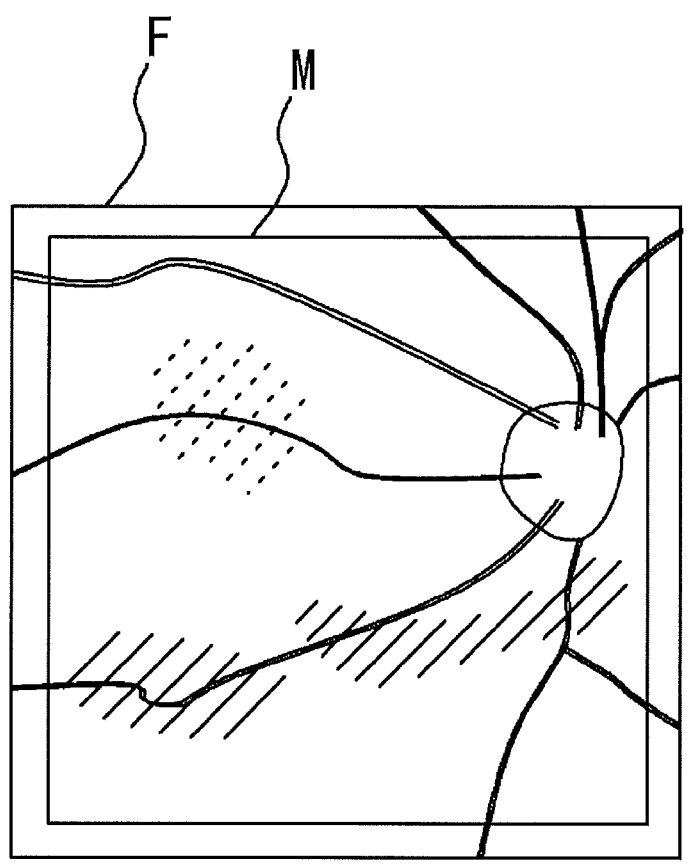
FIG. 5 is a diagram for explaining an example of a superimposed display of a front fundus image and the comparison map.

FIG. 5 is a diagram for explaining an example of the superimposed display of the front fundus image and the comparison map. For example, the control unit 70 superimposes the comparison map M on the front fundus image F via an image processing to associate the comparison map M with the front fundus image F. Then the control unit 70 displays a superimposed image of the comparison map M and the front fundus image F on the monitor 75. For example, in a case of performing the superimposed display, the control unit 70 generates an OCT front image from the three-dimensional tomographic image used for the analysis and associates the generated OCT front image with the comparison map M, thereby associating both the data in a pixel-to-pixel relation. The control unit 70 performs, for example, a matching between the generated OCT front image and the front fundus image obtained by the observation optical system 200 and adjusts a relative position between the comparison map and the front fundus image.

Incidentally in a case of simultaneously displaying the comparison map and the fundus observation image, such the display is not limited to the superimposed display. For example, the comparison map and the fundus observation image may be displayed in a juxtaposed manner, displayed on the same screen or displayed separately on individual monitors.

In this example, the examiner operates the operation unit 76 in the analysis mode and selects a not-shown ocular axial length value input switch. When the ocular axial length value input switch is operated, the control unit 70 displays an input screen capable of inputting an ocular axial length value on the monitor 75. The examiner operates the operation unit 76 and inputs an ocular axial length value. After inputting the ocular axial length value, the examiner selects a not-shown ocular axial length value input completion switch. When the examiner inputs the ocular axial length value, the control unit 70 acquires the ocular axial length value (S2). Incidentally the acquisition of the ocular axial length is not limited to the input by the examiner. For example, the control unit 70 may be arranged to be connected to the ocular axial length measurement apparatus and receive the ocular axial length value measured by the ocular axial length measurement apparatus. Alternatively, for example, the control unit 70 may be arranged to acquire the ocular axial length of the examinee from the memory or the device storing the ocular axial length value.

When the ocular axial length value is acquired, the control unit 70 selects one of the normal eye database and the long ocular axis database based on the acquired ocular axial length value. For example, the control unit 70 determines whether or not the ocular axial length value exceeds the threshold value (S3). For example, the threshold value may be set to a constant value or changeable optionally. For example, the threshold value is set to an ocular axial length value at the boundary between the ocular axial length range of the normal eye database and the ocular axial length range of the long ocular axis database. Of course, the setting of the threshold value is not limited to the setting to the ocular axial length value at the boundary. The examiner can set the threshold value to an optional ocular axial length value.

In this embodiment, an ocular axial length value (e.g., 26 mm) at the boundary between the ocular axial length range of the normal eye database and the ocular axial length range of the long ocular axis database is set as the threshold value.

In a case where the acquired ocular axial length value does not exceed the threshold value, the control unit 70 maintains a state of displaying the comparison map acquired referring to the normal eye database on the monitor 75. Alternatively, in a case where the acquired ocular axial length value exceeds the threshold value, the control unit 70 switches the database (S5). The control unit 70 acquires the long ocular axis database from the memory 72. The control unit 70 analyzes the detection result of the individual layers of the tomographic image acquired by referring to the long ocular axis database and acquires the comparison map (S6). The control unit 70 displays the acquired comparison map on the front fundus image in a superimposed manner (S7). Incidentally, although this embodiment is arranged to display the comparison map, this embodiment is not limited thereto. This embodiment may be arranged to display another analysis information. Further this embodiment may be arranged to display a plurality of analysis information.

Figure 6A:
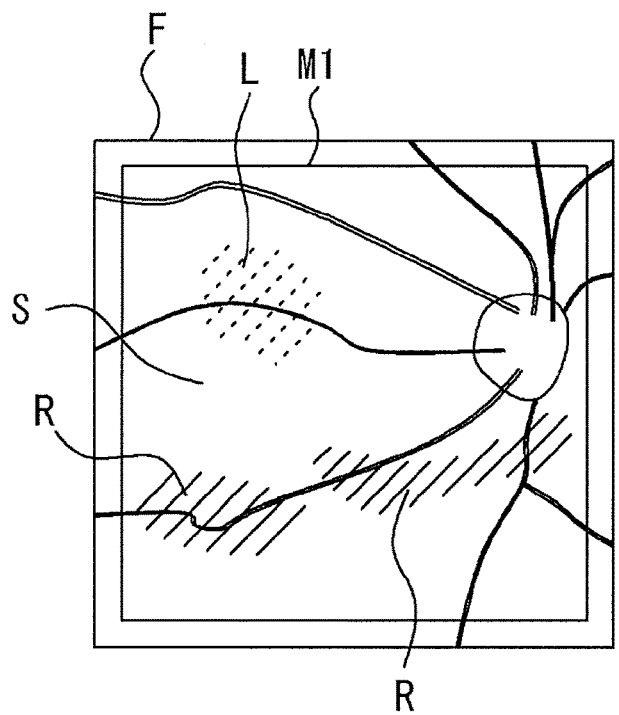
FIGS. 6A and 6B are diagrams for explaining the comparison map before and after the switching of a database.
Figure 6B:
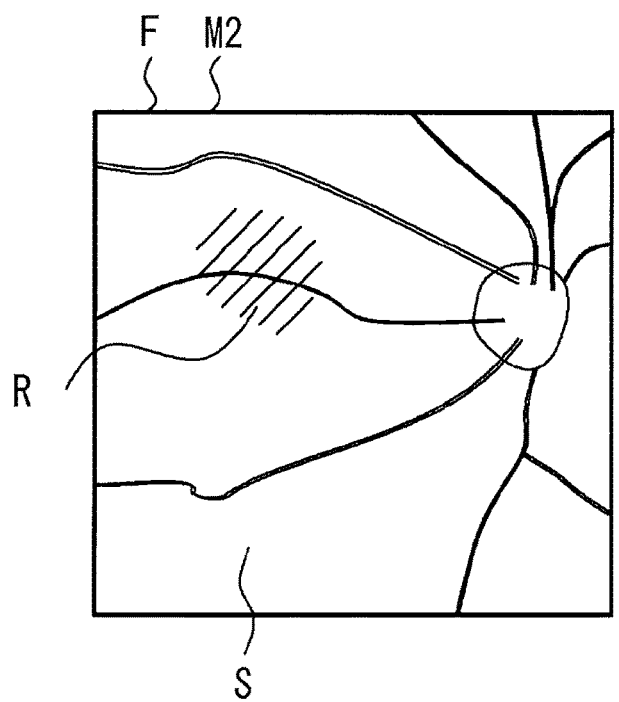

FIG. 6 is diagrams for explaining the comparison map before and after the switching of the database. For example, FIG. 6(a) shows the comparison map acquired referring to the normal eye database. For example, FIG. 6(b) shows the comparison map acquired referring to the long ocular axis database. By switching the database, a portion determined to be the abnormal portion L in the comparison map M1 acquired referring to the normal eye database may be determined to be the borderline portion R in the comparison map M2 acquired referring to the long ocular axis database. Also a portion determined to be the borderline portion L in the comparison map M1 acquired referring to the normal eye database may be determined to be the normal portion S in the comparison map M2 acquired referring to the long ocular axis database. In this manner, with respect to an examinee's eye having a long ocular axial length, the determination result according to the long ocular axial length can be confirmed by acquiring the comparison map referring to the long ocular axis database Incidentally the control unit 70 changes a display size of the comparison map at the time of displaying the comparison map on the front fundus image in the superimposed manner. That is, the control unit 70 changes the size of the comparison map M with respect to the front fundus image F together with the switching of the database. The comparison map represents the analysis result within the range stored in the database. In this embodiment, for example, the range acquiring the comparison map (analysis information) is processed in a similar range as the database. In this embodiment, for example, the front fundus image is acquired from an image within a range of 10.0×10.0 mm. The characteristic information of the normal eye database is acquired within a range of 9.5×9.5 mm. The characteristic information of the long ocular axis database is acquired within a range of 10.0×10.0 mm. The difference of the range between the normal eye database and the long ocular axis database is largely influenced by the ocular axial length. For example, in a case of the long ocular axis database, the examinees' eyes having the individual long ocular axial lengths are photographed and then the database is prepared. Thus when the examinee's eye having the long ocular axial length is photographed under a photographing condition (scanning area, scanning position, scanning pattern, etc.) at the time of photographing to prepare the normal eye database, as the ocular axial length is long, a range of the measurement light irradiated on the fundus becomes large. Thus in the case of the long ocular axis database, even if the photographing is performed under the same photographing condition as that of the normal eye database, the photographing range becomes large. As a result, the range of the database (a range of the layer thickness distribution of the database) differs depending on the database. Therefore, at the time of displaying the comparison map in the superimposed manner, the control unit 70 changes the size of the comparison map with respect to the front fundus image according to the range of the database.

For example, when the switching to the long ocular axis database is performed, the control unit 70 may change the size of the comparison map M2 acquired referring to the long ocular axis database so as to be larger than the size of the comparison map M1 acquired referring to the normal eye database, and display this comparison map changed in its size in the superimposed manner (see FIG. 6). Incidentally, although this embodiment is arranged to change the size of the comparison map as an example, the embodiment is not limited thereto. This embodiment may be arranged to change the size of the front fundus image.

Incidentally, although this embodiment is arranged that the range acquiring the comparison map (analysis information) is processed in the similar range as the database, the embodiment is not limited thereto. This embodiment may be arranged that the range acquiring the comparison map can be set optionally. Of course, the range acquiring the comparison map may be changed optionally. For example, the control unit 70 may perform the analysis within a range smaller than that of the database and acquire the comparison map.

As described above, the analysis information according to the ocular axial length can be acquired by using the long ocular axis database. Thus the examiner can more accurately diagnose whether the large difference from the normal eye database is caused by the long ocular axial length of the examinee's eye or illness of the examinee. Further as the analysis information according to various ocular axial lengths can be acquired by selectively using one of the normal eye database and the long ocular axis database, information useful for supporting @a diagnosis can be provided.

MODIFIED EXAMPLE

The technique disclosed in the embodiment can be applied to a follow-up photographing and utilized at a time of follow-up of the examinee's eye. Images of the same examinee's eye respectively photographed on different dates may be subjected to the analysis processing individually, and the analysis information of these images may be displayed. For example, in a case of subjecting each of the first and second tomographic images photographed on different dates to the analysis processing, the examiner can acquire the individual analysis information referring to the different databases.

For example, upon analysis of the follow-up photographing, the control unit 70 stores information relating to the examinee's eye and the photographing condition in the memory 72 so that the database used upon the analysis of the first tomographic image can be referred to. For example, the memory 72 stores the ocular axial length value of the examinee's eye measured at the same timing as the acquisition timing of the first tomographic image. The control unit 70 can access to the database which is referred to upon the analysis of the first tomographic image, with reference to the ocular axial length value of the examinee's eye measured at the same timing as the acquisition timing of the first tomographic image.

Upon analyzing the second tomographic image, the control unit 70 reads the information of the database which has been referred to upon the analysis of the first tomographic image. The control unit 70 acquires analysis information of the second tomographic image by referring to the database which has been referred to upon the analysis of the first tomographic image. In this case, if a state of the examinee's eye does not change, it is merely required to acquire the analysis information by referring to the database having been referred to upon the analysis of the first tomographic image. However, if the state of the examinee's eye changes with a lapse of time, it is preferable to select again the database to be referred to. For example, if the ocular axial length value of the examinee's eye changes, this changed value may exceed the range of the ocular axial length covered by the database having been referred to upon the analysis of the first tomographic image.

In this case, it is preferable to perform the switching to the different database and acquire the analysis information by referring to the different database. For example, in a case where the analysis information of the first tomographic image is acquired by referring to the normal eye database, the examiner operates the operation unit 76 and inputs the ocular axial length value upon analysis of the second tomographic image. The ocular axial length value to be inputted is, for example, the ocular axial length value of the examinee's eye measured at the same timing as the acquisition timing of the second tomographic image.

If the inputted ocular axial length value exceeds the range of the ocular axial length of the normal eye database, the control unit 70 acquires the analysis information referring to the long ocular axis database. Of course, even in a case where the ocular axial length value exceeds the range of the ocular axial length of the normal eye database, if the examiner does not perform the switching of the database via the operation of the operation unit 76, the control unit 70 may acquire the analysis information referring to the normal eye database. Of course, the control unit 70 may be arranged to acquire the individual analysis information of the second tomographic image by referring to both the normal eye database and the long ocular axis database, respectively. That is, the control unit may be arranged to acquire, with respect to each of the tomographic images photographed on different dates, a plurality of the analysis information by referring to a plurality of the databases, respectively. Although this embodiment is explained as to the case of using the two tomographic images as the tomographic images photographed on different dates, the embodiment is not limited thereto. The number of the tomographic images may be two or more.

Figure 7:
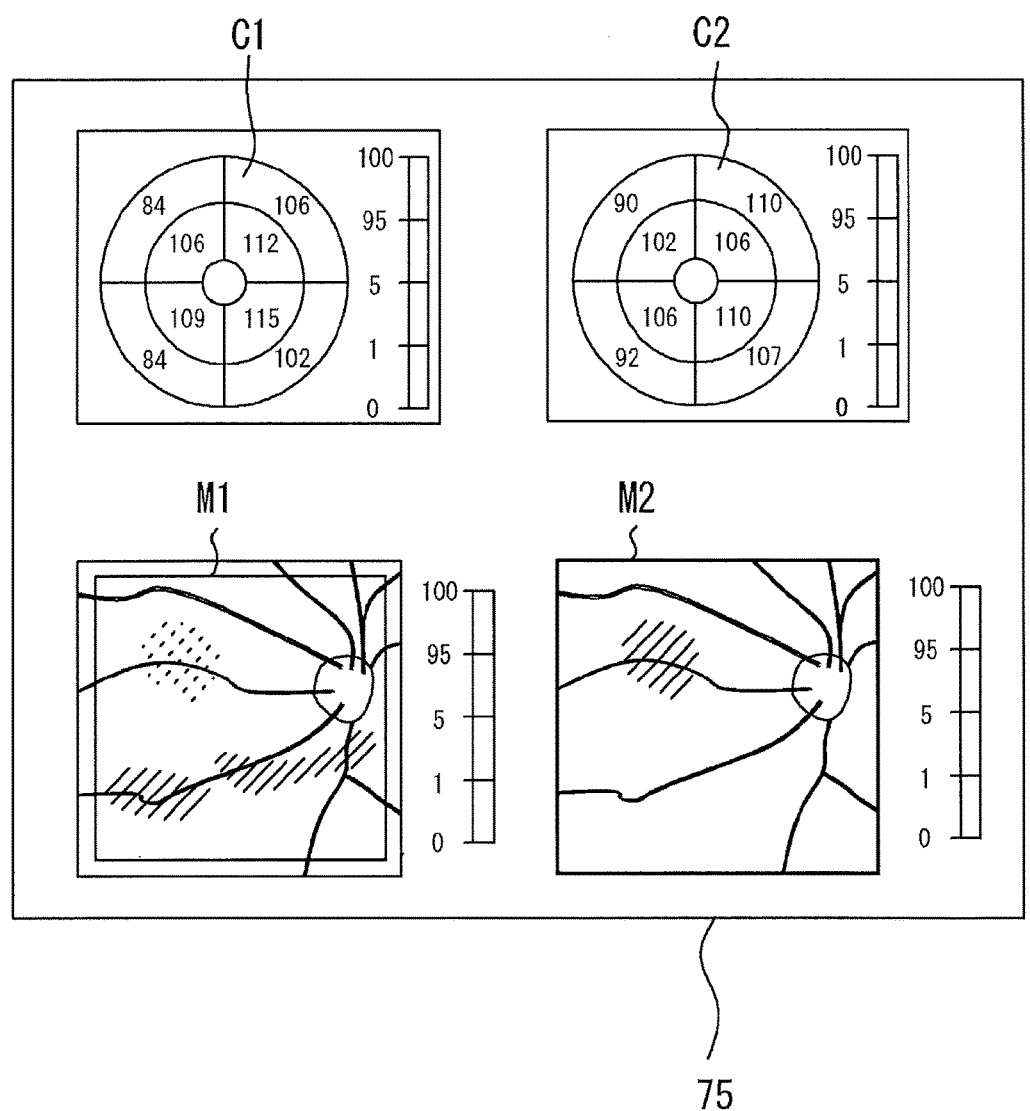
FIG. 7 is a diagram illustrating an example of an analysis screen at the time of a follow-up photographing.

The display method of the analysis information is merely required to be a display method capable of comparing the tomographic images photographed on different dates. For example, the individual analysis information of different photographing dates may be displayed in a juxtaposed manner. Further, the parameter (e.g., a layer thickens value, a difference value or the like) relating to the individual analysis information of different photographing dates may be displayed by a graph. FIG. 7 is a diagram illustrating an example of an analysis screen at the time of the follow-up photographing. As shown in Fi. 7, in this embodiment, the control unit 70 arranges the analysis information relating to the first tomographic image (comparison map M1) and the analysis information relating to the second tomographic image (comparison map M2) in a juxtaposed manner on the screen of the monitor 75. Further the control unit 70 displays, as the individual analysis information, an analysis chart C1 relating to the first tomographic image and an analysis chart C2 relating to the second tomographic image in a juxtaposed manner.

As described above, upon analysis of the follow-up photographing, the analysis information can be confirmed by switching the database according to the ocular axial length. Thus even if the ocular axial length changes in a case of photographing on different date, the diagnosis can be performed in a state of being coped with the change of the ocular axial length. Further, continuous observation becomes possible also with respect to the examinee's eye which is conventionally difficult to be observed continuously due to a fact that good analysis information cannot be acquired according to the change of ocular axial length. Further, as the examiner can acquire the analysis information using a plurality of the databases also with respect to a single tomographic image, the examiner can perform the diagnosis by taking more information into consideration.

In a case where the ocular axial length is acquired before the switching to the analysis mode, the control unit 70 may be arranged to, upon switching to the analysis mode, switch the database and acquire the analysis information based the ocular axial length acquired in advance. For example, if the ocular axial length value exceeds the ocular axial length range covered by the normal eye database, the control unit 70 switches to the analysis mode and acquires the analysis information referring to the long ocular axis database. The control unit 70 displays the acquired analysis information on the monitor 75. Of course, before the switching to the analysis mode, even if the ocular axial length value acquired in advance is within the ocular axial length range covered by the long ocular axis database, the control unit 70 may be arranged to acquire, upon switching to the analysis mode, the analysis information referring to the normal eye database.

Incidentally, in this embodiment, although the explanation is made as to the case where the normal eye database and the long ocular axis database are stored as the databases in the memory 72 and referred to, the embodiment is not limited thereto. The embodiment may be arranged to include further more databases. For example, the embodiment may be arranged to include the normal eye database, a first long ocular axis database and a second long ocular axis database. In this case, for example, the second long ocular axis database covers ocular axial length values longer than the range of the ocular axial length covered by the first long ocular axis database. In this manner, more detailed analysis information can be acquired by providing the databases to be referred to stepwise.

Incidentally, although the embodiment is arranged in a manner that the analysis information is switched and displayed. The embodiment may be arranged to acquire a plurality of the analysis information referring to the plurality of the databases with respect to the same tomographic image. For example, the control unit 70 acquires a plurality of the analysis information referring to the individual databases with respect to the tomographic image. According to such the configuration, the examiner can diagnose the examinee's eye by confirming the analysis information acquired referring to the various kinds of databases, and hence can perform the diagnosis easily.

In this embodiment, as an example, the control unit 70 is arranged to perform the switching operation of the database based on the ocular axial length value, but the embodiment is not limited thereto. The switching operation of the database can be executed by various kinds of methods. For example, a database changeover switch may be provided, and the control unit 70 may switch the database when the examiner operates the operation unit 76 and selects the database changeover switch.

Although this embodiment is configured to acquire the comparison map referring to the long ocular axis database, the embodiment is not limited thereto. The analysis information can be acquired referring to the long ocular axis database. For example, the analysis chart, the deviation map or the like can be acquired referring to the long ocular axis database. These analysis information is displayed together with the front fundus image in a superimposed manner. Incidentally the analysis information is not necessarily displayed in the superimposed manner. For example, the analysis information and the front fundus image may be displayed on the same screen of the monitor 75 without being displayed in the superimposed manner. Alternatively, for example, only the analysis information may be displayed on the monitor 75.

Incidentally, although the embodiment is explained as to the case where the size of the analysis map is changed upon the switching of the database, the embodiment is not limited thereto. The control unit 70 may change the display on the monitor 75 upon the switching of the database. For example, when the database is switched, the control unit 70 may change the display (change of the color, change of the character size, display of a mark of the corresponding database) so as to be able to discriminate the database referred to, at the time of acquiring the analysis information. Further, for example, the control unit 70 may be arranged to change the parameter relating to the analysis information upon the switching of the database. In this manner, as the display of the screen on the monitor is changed according to the switching of the database, the examiner can easily confirm the current analysis condition. Thus as the examiner is not required to newly confirm the analysis condition, labor, load, etc. of the examiner can be lightened. Further, it can be suppressed that the analysis information is acquired using the database different from that intended by the examiner.

Incidentally, although the embodiment is explained as to the case where the control unit 70 is arranged to change the display on the monitor 75 at the time of outputting the analysis information, the embodiment is not limited thereto. The control unit 70 is merely required to change a mode at the time of outputting the analysis information. For example, the control unit 70 may change a print mode at the time of printing the analysis information, for example. Alternatively, the control unit may change an output mode of the data (for example, change an image mode of the image data containing the analysis information) at the time of outputting the analysis information to the outside.

Incidentally, the embodiment may be arranged that, in a case where an examinee's eye for acquiring the analysis information does not satisfy the condition of the examinee's eye covered by the individual databases, informing representing that this examinee's eye is outside the applicable range of the databases may be displayed. For example, in a case of performing the analysis using the normal eye database, if the ocular axial length of the examinee's eye having been analyzed is outside the range of the ocular axial length of the normal eye database, at least one of an alarm display or an alarm color may be changed.

Incidentally, although the embodiment is arranged to analyze the three-dimensional tomographic image, the embodiment is not limited thereto. For example, an averaged image of the tomographic images at a predetermined scanning position may be acquired. Then layer thickness information may be acquired in an averaged image (B scan image) relating to a certain transversal direction, and an analysis of the layer at a predefined scanning line may be performed.

REFERENCE SIGNS LIST

1 fundus analysis device
10 fundus photographing device (optical coherence tomography device)
70 control unit
72 memory
75 monitor
76 operation unit
100 interference optical system (OCT optical system)
108 optical scanner
120 detector
200 front observation optical system
300 fixation target projection unit

What is claimed is:

1. A fundus analysis device comprising:
   a first database which stores layer thickness information of fundus relating to a plurality of eyes having respective long ocular axial lengths;

a second database which stores layer thickness information of fundus relating to a plurality of eyes each having different ocular axial lengths from the plurality of eyes of the first database; and a processor; and memory storing non-transitory computer readable instructions, when executed by the processor, causing the fundus analysis device to execute:

an acquisition instruction of acquiring a tomographic image of a fundus of an examinee's eye by an optical coherence tomography device;

a database switching instruction of controlling switching between the first database and the second database when a receiver of the fundus analysis device receives a database switch signal; and an analysis processing instruction of acquiring analysis information relating to layer thickness information of the fundus of the examinee's eye by referring to at least one of the first database and the second database.

2. The fundus analysis device according to claim 1, further comprising:

control means which changes a display mode on a monitor when the database switch instruction causes the fundus analysis device to perform switching between the first database and the second database.

3. The fundus analysis device according to claim 1, further comprising:

an operation device configured to receive an operation of a user and output the database switch signal in response to reception of the operation, wherein the database switch instruction causes the fundus analysis device to control the switching between the first database and the second database when the receiver receives the database switch signal outputted from the operation device in response to the reception of the operation of a user.

4. The fundus analysis device according to claim 3, wherein the non-transitory computer readable instructions causes the fundus analysis device to execute changing a display mode on a monitor when the receiver receives the database switch signal outputted from the operation device.

5. The fundus analysis device according to claim 1, wherein the tomographic image of the fundus of the examinee's eye acquired by the optical coherence tomography device is three-dimensional OCT data, and the analysis processing instruction causes the fundus analysis device to detect layer information in the three-dimensional OCT data via an image processing, and acquire an analysis map representing a two-dimensional distribution relating to the layer thickness information of the fundus of the examinee's eye by referring to the first database or the second database.

6. The fundus analysis device according to claim 5, wherein the data switch instruction causes the fundus analysis device to switch the database when the receiver receives the database switch signal outputted based on a value of the ocular axial length, and the non-transitory computer readable instructions causes the fundus analysis device to execute displaying a front image of the fundus of the examinee's eye acquired by front image acquisition instruction and the analysis map in a superimposed manner, and changing a size of the analysis map with respect to the front image.

7. The fundus analysis device according to claim 1, wherein with respect to the tomographic image of the examinee's eye, the analysis processing instruction causes the fundus analysis device to acquire first analysis information relating to the layer thickness information of the fundus of the examinee's eye referring to the first database and acquire second analysis information relating to the layer thickness information of the fundus of the examinee's eye referring to the second database:

the non-transitory computer readable instructions causes the fundus analysis device to display the first analysis information relating to the layer thickness information of the fundus of the examinee's eye and the second analysis information relating to the tomographic image on a same screen of a monitor.

8. The fundus analysis device according to claim 1, wherein the analysis processing instruction causes the fundus analysis device to acquire a plurality of the layer thickness information of the fundus of the examinee's eye obtained by photographing the tomographic image of the same examinee's eye at different timings, and acquire a plurality of the analysis information respectively corresponding to the plurality of layer thickness information by referring to at least one of the first and second databases, and the non-transitory computer readable instructions causes the fundus analysis device to display the plurality of the analysis information on a same screen of a monitor.

9. The fundus analysis device according to claim 1, wherein the non-transitory computer readable instructions causes the fundus analysis device to add identification information, for identifying one of the first and second databases having been referred to, in the analysis information in a case where the switching is performed between the first and second databases.

10. The fundus analysis device according to claim 1, wherein the non-transitory computer readable instructions causes the fundus analysis device to execute an ocular axial length value acquisition instruction of acquiring a value of the ocular axial length, and the data switch instruction causes the fundus analysis device to perform the switching between the first database and the second database based on the ocular axial length value acquired by the ocular axial length value acquisition instruction.

11. The fundus analysis device according to claim 1, wherein the analysis information includes information relating to a distance of layer boundaries corresponding to a predetermined retina layer.

12. A non-transitory computer readable recording medium storing a fundus analysis program executed by a processor of a fundus analysis device which includes a first database which stores layer thickness information of fundus relating to a plurality of eyes having respective long ocular axial length and a second database which stores layer thickness information of fundus relating to a plurality of eyes each having different ocular axial lengths from the plurality of eyes of the first database, the program, when executed by the processor, causing the fundus analysis device to execute:

an acquisition instruction of acquiring a tomographic image of a fundus of an examinee's eye acquired by an optical coherence tomography device;

a database switching instruction of controlling switching between the first database and the second database when a receiver of the fundus analysis device receives a database switch signal; and an analysis processing instruction of acquiring analysis information relating to layer thickness information of the fundus of the examinee's eye by referring to at least one of the first database and the second database.

\* \* \* \* \*